(12) United States Patent
Ascione et al.

(10) Patent No.: US 8,419,807 B2
(45) Date of Patent: Apr. 16, 2013

(54) COMPOSITION INCLUDING A GLYCERIDE AND AN ORGANOPHOSPHONIC ACID OR ONE OF THE SALTS THEREOF, DYEING OR COLOUR-LIGHTENING METHOD IMPLEMENTING SAME AND DEVICES

(75) Inventors: Jean-Marc Ascione, Paris (FR); Jean Cotteret, Maisons Laffite (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/501,532

(22) PCT Filed: Oct. 12, 2010

(86) PCT No.: PCT/FR2010/052158
§ 371 (c)(1),
(2), (4) Date: Apr. 12, 2012

(87) PCT Pub. No.: WO2011/045526
PCT Pub. Date: Apr. 21, 2011

(65) Prior Publication Data
US 2012/0199156 A1    Aug. 9, 2012

Related U.S. Application Data

(60) Provisional application No. 61/259,751, filed on Nov. 10, 2009.

(30) Foreign Application Priority Data

Oct. 13, 2009  (FR) ...................... 09 57176

(51) Int. Cl.
*A61Q 5/10* (2006.01)
(52) U.S. Cl.
USPC ............... 8/405; 8/406; 8/408; 8/435; 8/580; 8/584; 8/633
(58) Field of Classification Search ............... 8/405, 406, 8/408, 435, 580, 584, 633
See application file for complete search history.

(56) References Cited

U.S. PATENT DOCUMENTS

| | | |
|---|---|---|
| 3,869,454 A | 3/1975 | Lang et al. |
| 3,955,918 A | 5/1976 | Lang |
| 4,003,699 A | 1/1977 | Rose et al. |
| 4,025,301 A | 5/1977 | Lang |
| 4,138,478 A | 2/1979 | Reese et al. |
| RE30,199 E | 1/1980 | Rose et al. |
| 4,685,933 A | 8/1987 | Wolff et al. |
| 5,061,289 A | 10/1991 | Clausen et al. |
| 5,380,340 A | 1/1995 | Neunhoeffer et al. |
| 5,708,151 A | 1/1998 | Mockli |
| 5,766,576 A | 6/1998 | Lowe et al. |
| 6,099,592 A | 8/2000 | Vidal et al. |
| 6,238,653 B1 | 5/2001 | Narasimhan et al. |
| 6,338,741 B1 | 1/2002 | Vidal et al. |
| 6,554,872 B2 | 4/2003 | Genet et al. |
| 6,645,258 B2 | 11/2003 | Vidal et al. |
| 6,730,789 B1 | 5/2004 | Birault et al. |
| 6,881,230 B2 | 4/2005 | Vidal |
| 6,884,265 B2 | 4/2005 | Vidal et al. |
| 6,884,266 B2 | 4/2005 | Vidal et al. |
| 6,893,471 B2 | 5/2005 | Vidal |
| 6,986,795 B2 | 1/2006 | Genet et al. |
| 7,001,436 B2 | 2/2006 | Vidal et al. |
| 7,022,143 B2 | 4/2006 | Vidal et al. |
| 7,060,110 B2 | 6/2006 | Vidal et al. |
| 7,261,743 B2 | 8/2007 | Plos et al. |
| 7,311,736 B2 | 12/2007 | Burgaud et al. |
| 7,399,320 B2 | 7/2008 | Burgaud et al. |
| 7,407,516 B2 | 8/2008 | Vidal |
| 7,582,122 B2 | 9/2009 | Daubresse et al. |
| 7,909,887 B2 | 3/2011 | Hercouet |
| 2004/0105830 A1 | 6/2004 | Boswell et al. |
| 2006/0156490 A1 | 7/2006 | David et al. |
| 2006/0242773 A1 | 11/2006 | Kravtchenko et al. |
| 2007/0107143 A1* | 5/2007 | Boswell et al. .............. 8/405 |

FOREIGN PATENT DOCUMENTS

| | | |
|---|---|---|
| DE | 2359399 | 6/1975 |
| DE | 3843892 | 6/1990 |
| DE | 4133957 | 4/1993 |
| DE | 19543988 | 5/1997 |
| DE | 102006012575 | 2/2007 |
| DE | 102006020050 | 10/2007 |
| DE | 102006061830 | 6/2008 |
| EP | 0167952 | 1/1986 |

(Continued)

OTHER PUBLICATIONS

French Search Report for FR 2 951 080, Jun. 17, 2010, 2 pages.
Walter Noll, "Chemistry and Technology of Silicones," Academic Press, New York, San Francisco, London, pp. 1-23, 1968.
Charles Todd and Timothy Byers, "Volatile Silicone Fluids for Cosmetic Formulations," Cosmetics and Toiletries, vol. 91, pp. 29-32, Jan. 1976.
English language abstract of DE 102006012575, (2007).
English language abstract of EP 0770375, (1997).
English language abstract of EP 1433471, (1986).
English language abstract of EP 1433472, (2004).
English language abstract of EP 1433473, (2004).
English language abstract of EP 1433474, (2004).
English language abstract of EP 1619220, (2006).
English language abstract of EP 1619221, (2006).
English language abstract of EP 1634926, (2006).

(Continued)

*Primary Examiner* — Eisa Elhilo
(74) *Attorney, Agent, or Firm* — O'Brien Jones, PLLC.

(57) ABSTRACT

The present invention relates to a composition for coloring or lightening human keratin fibers, comprising, in a cosmetically medium: (a) at least 25 wt. % of one or more fatty substances; (b) one or more salified or unsalified organophosphonic acids; (c) one or more alkalizing agents and/or one or more dyes selected from oxidation dyes, direct dyes and mixtures thereof and (d) one or more oxidizing agents. It further relates to a method of coloring or lightening employing it. Another object of the invention is constituted by kits with two or three compartments for obtaining, after mixing the compositions from the compartments, just before its application, a composition according to the invention.

21 Claims, No Drawings

FOREIGN PATENT DOCUMENTS

| | | |
|---|---|---|
| EP | 0714954 | 6/1996 |
| EP | 0770375 | 5/1997 |
| EP | 1006153 | 6/2000 |
| EP | 1377261 | 1/2004 |
| EP | 1377262 | 1/2004 |
| EP | 1377263 | 1/2004 |
| EP | 1377264 | 1/2004 |
| EP | 1378544 | 1/2004 |
| EP | 1399116 | 3/2004 |
| EP | 1399117 | 3/2004 |
| EP | 1399425 | 3/2004 |
| EP | 1408919 | 4/2004 |
| EP | 1416909 | 5/2004 |
| EP | 1433471 | 6/2004 |
| EP | 1433472 | 6/2004 |
| EP | 1433473 | 6/2004 |
| EP | 1433474 | 6/2004 |
| EP | 1619220 | 1/2006 |
| EP | 1619221 | 1/2006 |
| EP | 1634926 | 3/2006 |
| EP | 1637566 | 3/2006 |
| EP | 1671951 | 6/2006 |
| EP | 1671954 | 6/2006 |
| EP | 1671955 | 6/2006 |
| EP | 1672033 | 6/2006 |
| EP | 1674073 | 6/2006 |
| EP | 1679312 | 7/2006 |
| EP | 1757660 | 2/2007 |
| EP | 2072036 | 6/2009 |
| FR | 2140205 | 1/1973 |
| FR | 2189006 | 1/1974 |
| FR | 2285851 | 4/1976 |
| FR | 2733749 | 11/1996 |
| FR | 2801308 | 5/2001 |
| FR | 2886136 | 12/2006 |
| GB | 1026978 | 4/1966 |
| GB | 1153196 | 5/1969 |
| JP | 2-19576 | 1/1990 |
| JP | 5-163124 | 6/1993 |
| WO | 94/08969 | 4/1994 |
| WO | 94/08970 | 4/1994 |
| WO | 95/01772 | 1/1995 |
| WO | 95/15144 | 6/1995 |
| WO | 96/15765 | 5/1996 |
| WO | 2005/055966 | 6/2005 |
| WO | 2006/063866 | 6/2006 |
| WO | 2006/063867 | 6/2006 |
| WO | 2006/063869 | 6/2006 |

OTHER PUBLICATIONS

English language abstract of EP 1637566, (2006).
English language abstract of EP 1671951, (2006).
English language abstract of EP 1671954, (2006).
English language abstract of EP 1671955, (2006).
English language abstract of EP 1672033, (2006).
English language abstract of EP 1674073, (2006).
English language abstract of FR 2886136, (2006).
English language abstract of JP 2-19576, (1990).
English language abstract of JP 5-163124, (1993).
English language abstract of DE 102006061830, (2008).
English language abstract of DE 102006020050, (2007).

* cited by examiner

COMPOSITION INCLUDING A GLYCERIDE AND AN ORGANOPHOSPHONIC ACID OR ONE OF THE SALTS THEREOF, DYEING OR COLOUR-LIGHTENING METHOD IMPLEMENTING SAME AND DEVICES

This is a national stage application of PCT/FR2010/052158, filed internationally on Oct. 12, 2010, which claims priority to French Application No. 0957176, filed on Oct. 13, 2009, and U.S. Provisional Patent Application No. 61/259,751, filed on Nov. 10, 2009, the entire contents of each of which are incorporated by reference herein.

The present invention relates to a composition for colouring or lightening human keratin fibres comprising at least one oxidizing agent, a high fatty substance content, at least one organophosphonic acid or a salt thereof and at least one dye selected from direct dyes, oxidation dyes or mixtures thereof and/or at least one alkalizing agent. The invention also relates to a method of colouring or lightening employing it as well as multi-compartment kits.

Among the methods for colouring human keratin fibres, such as the hair, we may mention oxidation dyeing or permanent dyeing. More particularly, this form of colouring employs one or more oxidation dyes, usually one or more oxidation bases optionally combined with one or more couplers.

In general, oxidation bases are selected from ortho- or para-phenylenediamines, ortho- or para-aminophenols as well as heterocyclic compounds. These oxidation bases are colourless or weakly-coloured compounds which, when combined with oxidizing products, give coloured species.

Quite often, the shades obtained with these oxidation bases are varied by combining them with one or more couplers, the latter being selected notably from aromatic meta-diamines, meta-aminophenols, meta-diphenols and certain heterocyclic compounds, such as indole compounds.

The variety of molecules employed as oxidation bases and couplers provides a rich palette of colours.

Direct or semi-permanent dyeing is also known. The method conventionally used in direct dyeing consists of applying, on the keratin fibres, direct dyes which are coloured and colouring molecules, having an affinity for fibres, pausing, and then rinsing.

The direct dyes generally used are selected from benzene, anthraquinone, nitropyridine, azo, methine, azomethine, xanthene, acridine, azine and triarylmethane nitro direct dyes.

This type of method does not require the use of an oxidizing agent for developing the colouring. However, its use is not ruled out for obtaining a lightening effect along with the colouring. This is then called direct or semi-permanent colouring in lightening conditions.

The methods of permanent or semi-permanent colouring in lightening conditions therefore consist of using, with the dyeing composition, an aqueous composition comprising at least one oxidizing agent, at alkaline pH in the vast majority of cases. The purpose of this oxidizing agent is, among other things, to break down the melanin in the hair, which, depending on the nature of oxidizing agent present, leads to more or less pronounced lightening of the fibres. Thus, for a relatively low degree of lightening, the oxidizing agent is generally hydrogen peroxide. When a greater degree of lightening is required, usually peroxidized salts are employed, such as persulphates for example, in the presence of hydrogen peroxide.

There is a need for satisfactory efficacy of the lightening and colouring products, notably in terms of lightening power or intensity of colouring and/or selectivity, while lessening the harmful effects connected with the simultaneous presence of alkaline agents and oxidizing agents such as hydrogen peroxide. These harmful effects mainly relate to the degradation of keratin fibres and to the odours of the alkaline agents employed, such as ammonia and amines.

It is therefore sought to enhance the effects of the alkaline agents and/or of the oxidizing agents so as to limit their concentrations while having maximum dyeing or lightening efficacy.

The aim of the present invention is to obtain compositions for oxidation dyeing or lightening of keratin fibres that are more satisfactory with respect to these points.

This aim and others are achieved by the present invention, which therefore relates to a composition for colouring or lightening human keratin fibres, comprising, in a cosmetically acceptable medium:

(a) at least 25 wt. % of one or more fatty substances;
(b) one or more salified or unsalified organophosphonic acids;
(c) one or more alkalizing agents and/or one or more dyes selected from oxidation dyes, direct dyes and mixtures thereof;
(d) one or more oxidizing agents.

It also relates to a method of colouring or lightening human keratin fibres, consisting of employing the aforementioned composition.

The invention further relates to a kit with two compartments comprising in one, a first composition containing one or more fatty substances, one or more alkalizing agents and/or one or more dyes selected from oxidation dyes, direct dyes and mixtures thereof; and in the other, a second composition containing one or more oxidizing agents; the first and/or the second composition comprising one or more salified or unsalified organophosphonic acids, the compositions of the two compartments being intended to be mixed to give the composition according to the invention, just before application on human keratin fibres.

The invention relates finally to a kit with three compartments comprising in one, a first composition containing one or more fatty substances; in another, a second composition containing one or more alkalizing agents and/or one or more dyes selected from oxidation dyes, direct dyes or mixtures thereof; and in the last, a third composition containing one or more oxidizing agents; the first and/or second and/or third composition comprising one or more salified or unsalified organophosphonic acids, the compositions of the three compartments being intended to be mixed to give the composition according to the invention, just before application on human keratin fibres.

Other characteristics and advantages of the invention will become clearer on reading the description and the examples given below.

Hereinafter, and unless stated otherwise, the limits of a range of values are included in this range.

The human keratin fibres treated by the method according to the invention are preferably the hair.

As already mentioned, the colouring composition according to the invention comprises at least 25 wt. % of one or more fatty substances, preferably at least 30 wt. %.

"Fatty substance(s)" means an organic compound that is insoluble in water at normal temperature (25° C.) and at atmospheric pressure (760 mmHg; i.e. $1.013 \cdot 10^5$ Pa) (solubility below 5% and preferably below 1% and more preferably below 0.1%). They have in their structure at least one hydrocarbon chain having at least 6 carbon atoms or a sequence of at least two siloxane groups. Moreover, fatty substances are soluble in organic solvents in the same conditions of temperature and pressure, for example chloroform, ethanol or benzene.

According to the invention, the fatty substances are selected from compounds that are liquid or pasty at room temperature and at atmospheric pressure.

More particularly, fatty substances are selected from $C_6$-$C_{16}$ lower alkanes, non-silicone oils of animal, vegetable or synthetic origin, hydrocarbons of mineral or synthetic origin, fluorinated oils, fatty alcohols, fatty acids, esters of fatty acid and/or of fatty alcohol, non-silicone waxes, silicones.

It should be noted that in the sense of the invention, the alcohols, esters and fatty acids have more particularly at least one linear or branched, saturated or unsaturated hydrocarbon group, comprising 6 to 30 carbon atoms, optionally substituted, in particular with one or more hydroxyl groups (in particular 1 to 4). If they are unsaturated, these compounds can comprise one to three, conjugated or unconjugated, carbon-carbon double bonds.

As for the lower alkanes, the latter comprise from 6 to 16 carbon atoms, and are linear or branched, optionally cyclic. As examples, we may mention hexane, dodecane, the isoparaffins such as isohexadecane and isodecane.

As non-silicone oils of animal, vegetable or synthetic origin, usable in the composition of the invention, we may mention for example:

hydrocarbon oils of animal origin, such as perhydrosqualene;

triglyceride oils of vegetable or synthetic origin, such as the liquid triglycerides of fatty acids having from 6 to 30 carbon atoms such as the triglycerides of heptanoic or octanoic acids, or for example sunflower oil, maize oil, soya oil, cucurbit oil, grapeseed oil, sesame oil, hazelnut oil, apricot oil, macadamia oil, arara oil, castor oil, avocado oil, triglycerides of caprylic/capric acids such as those sold by the company Stearineries Dubois or those sold under the designations Miglyol® 810, 812 and 818 by the company Dynamit Nobel, jojoba oil, karite butter oil;

linear or branched hydrocarbons, of mineral or synthetic origin with more than 16 carbon atoms, such as volatile or non-volatile paraffin oils, and their derivatives, petroleum jelly, liquid paraffin, polydecenes, hydrogenated polyisobutene such as Parleam®;

fluorinated oils such as perfluoromethylcyclopentane and perfluoro-1,3-dimethylcyclohexane, sold under the designations "FLUTEC® PC1" and "FLUTEC® PC3" by the company BNFL Fluorochemicals; perfluoro-1,2-dimethylcyclobutane; perfluoroalkanes such as dodecafluoropentane and tetradecafluorohexane, sold under the designations "PF 5050®" and "PF 5060®" by the company 3M, or bromoperfluorooctyl sold under the designation "FORALKYL®" by the company Atochem; nonafluoromethoxybutane and nonafluoroethoxyisobutane; derivatives of perfluoromorpholine, such as 4-trifluoromethyl perfluoromorpholine sold under the designation "PF 5052®" by the company 3M.

The fatty alcohols suitable for the application of the invention are more particularly selected from saturated or unsaturated, linear or branched alcohols, having from 8 to 30 carbon atoms. We may mention for example cetyl alcohol, stearyl alcohol and their mixture (cetylstearyl alcohol), octyldodecanol, 2-butyloctanol, 2-hexyldecanol, 2-undecylpentadecanol, oleic alcohol and linoleic alcohol.

The fatty acids usable within the scope of the invention are more particularly selected from saturated or unsaturated carboxylic acids, having from 6 to 30 carbon atoms, in particular from 9 to 30 carbon atoms. They are advantageously selected from myristic acid, palmitic acid, stearic acid, behenic acid, oleic acid, linoleic acid, linolenic acid and isostearic acid.

With regard to the esters of fatty acid and/or of fatty alcohols, advantageously different from the triglycerides mentioned above, we may mention notably the esters of $C_1$-$C_{26}$ aliphatic mono- or polyacids which are saturated or unsaturated, linear or branched and of $C_1$-$C_{26}$ aliphatic mono- or polyalcohols which are saturated or unsaturated, linear or branched, the total number of carbons of the esters being greater than or equal to 10.

Among the monoesters, we may mention dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, ethyl-2-hexyl palmitate, 2-octyldecyl palmitate, alkyl myristates such as isopropyl, butyl, cetyl, 2-octyldodecyl, mirystyl and stearyl myristate, hexyl stearate, butyl stearate, isobutyl stearate; dioctyl malate, hexyl laurate, 2-hexyldecyl laurate.

Still within the scope of this variant, it is also possible to use esters of $C_4$-$C_{22}$ di- or tricarboxylic acids and of $C_1$-$C_{22}$ alcohols and esters of mono-, di- or tricarboxylic acids and of $C_2$-$C_{26}$ di-, tri-, tetra- or pentahydroxy alcohols.

We may notably mention: diethyl sebacate; diisopropyl sebacate; diisopropyl adipate; di-n-propyl adipate; dioctyl adipate; diisostearyl adipate; dioctyl maleate; glyceryl undecylate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisanonate; and polyethylene glycol distearates.

Among the esters mentioned above, it is preferable to use ethyl, isopropyl, myristyl, cetyl and stearyl palmitates, ethyl-2-hexyl palmitate, 2-octyldecyl palmitate, alkyl myristates such as isopropyl, butyl, cetyl, 2-octyldodecyl myristate, hexyl stearate, butyl stearate, isobutyl stearate; dioctyl malate, hexyl laurate, 2-hexyldecyl laurate and isononyl isononanate, cetyl octanoate.

The composition can also comprise, as fatty ester, esters and di-esters of sugars of $C_6$-$C_{30}$ fatty acids, preferably $C_{12}$-$C_{22}$ fatty acids. It should be noted that "sugar" means oxygenated hydrocarbon compounds that have several alcohol functions, with or without aldehyde or ketone function, and that have at least 4 carbon atoms. These sugars can be monosaccharides, oligosaccharides or polysaccharides.

As suitable sugars, we may mention for example sucrose (or saccharose), glucose, galactose, ribose, fucose, maltose, fructose, mannose, arabinose, xylose, lactose, and their derivatives, notably alkylated, such as methylated derivatives such as methylglucose.

The esters of sugars and of fatty acids can be selected notably from the group comprising the esters or mixtures of esters of sugars described previously and of $C_6$-$C_{30}$ fatty acids, preferably $C_{12}$-$C_{22}$ fatty acids, linear or branched, saturated or unsaturated. If they are unsaturated, these compounds can comprise one to three, conjugated or unconjugated, carbon-carbon double bonds.

The esters according to this variant can also be selected from the mono-, di-, tri- and tetra-esters, polyesters and mixtures thereof.

These esters can be for example oleate, laurate, palmitate, myristate, behenate, cocoate, stearate, linoleate, linolenate, caprate, arachidonates, or mixtures thereof such as notably the oleopalmitate, oleostearate, palmitostearate mixed esters.

More particularly, the mono- and diesters are used and notably mono- or di-oleate, stearate, behenate, oleopalmitate, linoleate, linolenate, oleostearate, of sucrose, of glucose or of methylglucose.

We may mention as an example the product sold under the designation Glucate® DO by the company Amerchol, which is a methylglucose dioleate.

We may also mention as examples of esters or of mixtures of esters of sugar of fatty acid:
the products sold under the designations F160, F140, F110, F90, F70, SL40 by the company Crodesta, denoting respectively palmitostearates of sucrose formed from 73% of monoester and 27% of di- and triester, from 61% of monoester and 39% of di-, tri-, and tetraester, from 52% of monoester and 48% of di-, tri-, and tetraester, from 45% of monoester and 55% of di-, tri-, and tetraester, from 39% of monoester and 61% of di-, tri-, and tetraester, and sucrose monolaurate;
the products sold under the designation Ryoto Sugar Esters for example with the reference B370 and corresponding to sucrose behenate formed from 20% of monoester and 80% of ditriesterpolyester;
the sucrose monodipalmitostearate marketed by the company Goldschmidt under the designation Tegosoft® PSE.

The wax or waxes (non-silicone) are notably selected from carnauba wax, candelilla wax, and alfa wax, paraffin wax, ozokerite, vegetable waxes such as olive wax, rice wax, hydrogenated jojoba wax or absolute flower waxes such as the essential wax of blackcurrant flower sold by the company BERTIN (France), animal waxes such as beeswaxes, or modified beeswaxes (Cera Bellina); other waxes or waxy raw materials usable according to the invention are notably marine waxes such as that sold by the company SOPHIM under reference M82, waxes of polyethylene or of polyolefins in general.

The silicones usable in the cosmetic compositions of the present invention are volatile or non-volatile silicones, cyclic, linear or branched, unmodified or modified with organic groups, having a viscosity from $5.10^{-6}$ to 2.5 m$^2$/s at 25° C. and preferably $1.10^{-5}$ to 1 m$^2$/s.

The silicones usable according to the invention can be in the form of oils, waxes, resins or gums.

Preferably, the silicone is selected from the polydialkylsiloxanes, notably polydimethylsiloxanes (PDMS), and the organo-modified polysiloxanes having at least one functional group selected from the poly(oxyalkylene) groups, amine groups and alkoxy groups.

The organopolysiloxanes are defined in more detail in the work of Walter NOLL "Chemistry and Technology of Silicones" (1968), Academic Press. They can be volatile or non-volatile.

When they are volatile, the silicones are more particularly selected from those having a boiling point between 60° C. and 260° C., and even more particularly from:
(i) the cyclic polydialkylsiloxanes having from 3 to 7, preferably from 4 to 5 silicon atoms. These are, for example, octamethylcyclotetrasiloxane notably marketed under the name VOLATILE SILICONE® 7207 by UNION CARBIDE or SILBIONE® 70045 V2 by RHODIA, decamethylcyclopentasiloxane marketed under the name VOLATILE SILICONE® 7158 by UNION CARBIDE, and SILBIONE® 70045 V5 by RHODIA, and mixtures thereof.

We may also mention the cyclocopolymers of the dimethylsiloxanes/methylalkylsiloxane type, such as SILICONE VOLATILE® FZ 3109 marketed by the company UNION CARBIDE, of formula:

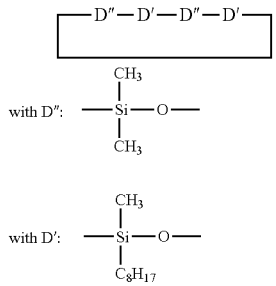

We may also mention the mixtures of cyclic polydialkylsiloxanes with organic silicon derivatives, such as the mixture of octamethylcyclotetrasiloxane and tetratrimethylsilylpentaerythritol (50/50) and the mixture of octamethylcyclotetrasiloxane and oxy-1,1'-(hexa-2,2,2',2',3,3'-trimethylsilyloxy) bisneopentane;
(ii) the volatile linear polydialkylsiloxanes having 2 to 9 silicon atoms and with a viscosity less than or equal to $5.10^{-6}$ m$^2$/s at 25° C. An example is decamethyltetrasiloxane notably marketed under the designation "SH 200" by the company TORAY SILICONE. Silicones included in this class are also described in the article published in Cosmetics and Toiletries, Vol. 91, January 76, pp. 27-32—TODD & BYERS "Volatile Silicone fluids for cosmetics".

Non-volatile polydialkylsiloxanes, gums and resins of polydialkylsiloxanes, polyorganosiloxanes modified with the above organofunctional groups, and mixtures thereof, are preferably used.

These silicones are more particularly selected from the polydialkylsiloxanes among which we may mainly mention polydimethylsiloxanes with trimethylsilyl end groups. The viscosity of the silicones is measured at 25° C. according to standard ASTM 445 Appendix C.

Among these polydialkylsiloxanes, we may mention non-limitatively the following commercial products:
the SILBIONE® oils of the series 47 and 70 047 or the MIRASIL® oils marketed by RHODIA such as, for example, the oil 70 047 V 500 000;
the oils of the MIRASIL® series marketed by the company RHODIA;
the oils of the 200 series from the company DOW CORNING such as DC200 having a viscosity of 60 000 mm$^2$/s;
the VISCASIL® oils from GENERAL ELECTRIC and some of the oils of the SF series (SF 96, SF 18) from GENERAL ELECTRIC.

We may also mention the polydimethylsiloxanes with dimethylsilanol end groups known by the name dimethiconol (CTFA), such as the oils of the 48 series from the company RHODIA.

In this class of polydialkylsiloxanes, we may also mention the products marketed under the designations "ABIL WAX® 9800 and 9801" by the company GOLDSCHMIDT, which are polydialkyl($C_1$-$C_{20}$) siloxanes.

The silicone gums usable according to the invention are notably polydialkylsiloxanes, preferably polydimethylsiloxanes having high number-average molecular weights between 200 000 and 1 000 000 used alone or mixed in a solvent. This solvent can be selected from volatile silicones, polydimethylsiloxane oils (PDMS), polyphenylmethylsiloxane oils (PPMS), isoparaffins, polyisobutylenes, methylene chloride, pentane, dodecane, tridecane or mixtures thereof.

Products more particularly usable according to the invention are mixtures such as:

mixtures formed from a chain-end hydroxylated polydimethylsiloxane, or dimethiconol (CTFA) and from a cyclic polydimethylsiloxane also called cyclomethicone (CTFA) such as the product Q2 1401 marketed by the company DOW CORNING;

mixtures of a polydimethylsiloxane gum and of a cyclic silicone such as the product SF 1214 Silicone Fluid from the company GENERAL ELECTRIC, this product is a gum SF 30 corresponding to a dimethicone, having a number-average molecular weight of 500 000 dissolved in oil SF 1202 Silicone Fluid corresponding to decamethylcyclopentasiloxane;

mixtures of two PDMS of different viscosities, and more particularly of a PDMS gum and a PDMS oil, such as the product SF 1236 from the company GENERAL ELECTRIC. The product SF 1236 is a mixture of a gum SE 30 defined above having a viscosity of 20 m²/s and of an oil SF 96 with a viscosity of $5.10^{-6}$ m²/s. This product preferably has 15% of gum SE 30 and 85% of an oil SF 96.

The resins of organopolysiloxanes usable according to the invention are crosslinked siloxane systems containing the units:

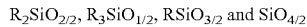

$R_2SiO_{2/2}$, $R_3SiO_{1/2}$, $RSiO_{3/2}$ and $SiO_{4/2}$ in which R represents an alkyl having 1 to 16 carbon atoms. Among these products, those particularly preferred are those in which R denotes a $C_1$-$C_4$ lower alkyl group, more particularly methyl.

We may mention among these resins the product marketed under the designation "DOW CORNING 593" or those marketed under the designations "SILICONE FLUID SS 4230 and SS 4267" by the company GENERAL ELECTRIC and which are silicones of dimethyl/trimethyl siloxane structure.

We may also mention the resins of the trimethylsiloxysilicate type notably marketed under the designations X22-4914, X21-5034 and X21-5037 by the company SHIN-ETSU.

The organomodified silicones usable according to the invention are silicones as defined previously and having in their structure one or more organofunctional groups fixed by a hydrocarbon group.

As well as the silicones described above, the organomodified silicones can be polydiaryl siloxanes, notably polydiphenylsiloxanes, and polyalkylarylsiloxanes functionalized by the organofunctional groups mentioned previously.

The polyalkarylsiloxanes are selected in particular from the polydimethyl/methylphenylsiloxanes, the linear and/or branched polydimethyl/diphenylsiloxanes with a viscosity in the range from $1.10^{-5}$ to $5.10^{-2}$ m²/s at 25° C.

Among these polyalkarylsiloxanes we may mention for example the products marketed under the following designations:

the SILBIONE® oils of the 70 641 series from RHODIA;
the oils of the RHODORSIL® series 70 633 and 763 from RHODIA;
the oil DOW CORNING 556 COSMETIC GRAD FLUID from DOW CORNING;
the silicones of the PK series from BAYER such as the product PK20;
the silicones of series PN, PH from BAYER such as the products PN1000 and PH1000;
certain oils of the SF series from GENERAL ELECTRIC such as SF 1023, SF 1154, SF 1250, SF 1265.

Among the organomodified silicones, we may mention the polyorganosiloxanes with:

polyethyleneoxy and/or polypropyleneoxy groups optionally comprising $C_6$-$C_{24}$ alkyl groups such as the products called dimethicone copolyol marketed by the company DOW CORNING under the designation DC 1248 or the oils SILWET® L 722, L 7500, L 77, L 711 from the company UNION CARBIDE and the alkyl($C_{12}$)-methicone copolyol marketed by the company DOW CORNING under the designation Q2 5200;

amino groups, substituted or unsubstituted, such as the products marketed under the designation GP 4 Silicone Fluid and GP 7100 by the company GENESEE or the products marketed under the designations Q2 8220 and DOW CORNING 929 or 939 by the company DOW CORNING. The substituted amino groups are in particular $C_1$-$C_4$ aminoalkyl groups;

alkoxylated groups, such as the product marketed under the designation "SILICONE COPOLYMER F-755" by SWS SILICONES and ABIL WAX® 2428, 2434 and 2440 by the company GOLDSCHMIDT.

More particularly, the fatty substances are selected from compounds that are liquid or pasty at room temperature and at atmospheric pressure.

Preferably, the fatty substance is a compound that is liquid at a temperature of 25° C. and at atmospheric pressure.

The fatty substances are preferably selected from $C_6$-$C_{16}$ lower alkanes, fatty alcohols, esters of fatty acid, esters of fatty alcohol, oils, in particular non-silicone mineral, vegetable and synthetic oils, hydrocarbon oils of mineral or synthetic origin, silicones. According to a more preferred embodiment, the fatty substance(s) is/are selected from $C_6$-$C_{16}$ lower alkanes, non-silicone oil of synthetic origin, hydrocarbon oils of mineral or synthetic origin, fatty alcohols, or their mixtures.

Preferably, the fatty substance is selected from liquid paraffin, polydecenes, liquid fatty alcohols and mixtures thereof.

The composition according to the invention comprises at least 25 wt. % of fatty substance(s), more particularly at least 30 wt. %. The composition according to the invention has more particularly a fatty substance content in the range from 25 to 80 wt. %, even more preferably from 25 to 65 wt. %, better still from 30 to 55 wt. % relative to the weight of the composition.

In the sense of the present invention organophosphonic acid means an organic compound having in its chemical structure one or more groups —$P(OH)_2$=O.

The salts of these acids are preferably the salts of alkali metals or alkaline-earth metals and in particular the salts of sodium or of potassium, ammonium salts, salts of organic amines and in particular of alkanolamines.

As phosphonic acids suitable for the invention we may mention, alone or mixed:

2-aminoethylphosphonic acid
dimethyl methylphosphonic acid
1-hydroxy ethylidene-1,1-diphosphonic acid
amino tris(methylene phosphonic) acid
ethylenediamine tetra(methylene phosphonic) acid
tetramethylenediamine tetra(methylene phosphonic) acid
hexamethylenediamine tetra(methylene phosphonic) acid
diethylenetriamine penta(methylene phosphonic) acid
phosphonobutane tricarboxylic acid
N-(phosphonomethyl)iminodiacetic acid 2-carboxyethyl phosphonic acid
2-hydroxyphosphonocarboxylic acid
amino-trismethylene phosphonic acid.

Preferably the organophosphonic acid(s) are selected from the compounds having at least two groups —P(OH)$_2$=O in their structure.

Even more preferably the organophosphonic acid is 1-hydroxy ethylidene-1,1-diphosphonic acid (HEDP) more commonly called etidronic acid.

In the composition of the invention the organophosphonic acid(s) preferably represent from 0.001 to 10 wt. %, better still from 0.002 to 1 wt. %, relative to the total weight of the composition.

As stated previously, the composition according to the invention comprises at least one dye selected from oxidation dyes, direct dyes or mixtures thereof and/or at least one alkalizing agent.

The oxidation dyes are in general selected from one or more oxidation bases optionally combined with one or more couplers.

As examples, the oxidation bases are selected from para-phenylenediamines, bisphenylalkylenediamines, para-aminophenols, ortho-aminophenols, heterocyclic bases and their salts of addition.

Among the para-phenylenediamines, we may mention as examples: para-phenylenediamine, para-toluoylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino N,N-diethyl 3-methyl aniline, N,N-bis(β-hydroxyethyl)-para-phenylenediamine, 4-N,N-bis(β-hydroxyethyl)amino 2-methyl aniline, 4-N,N-bis(β-hydroxyethyl)amino 2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl 3-methyl-para-phenylenediamine, N,N-(ethyl, β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino 5-aminotoluene, 3-hydroxy 1-(4'-aminophenyl)pyrrolidine and their salts of addition with an acid.

Among the para-phenylenediamines mentioned above, para-phenylenediamine, para-toluoylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and their salts of addition with an acid are particularly preferred.

Among the bisphenylalkylenediamines, we may mention as examples: N,N'-bis(β-hydroxyethyl) N,N'-bis(4'-aminophenyl) 1,3-diaminopropanol, N,N'-bis(β-hydroxyethyl) N,N'-bis(4'-aminophenyl)ethylenediamine, N,N'-bis(4-aminophenyl) tetramethylenediamine, N,N'-bis(β-hydroxyethyl) N,N'-bis(4-aminophenyl) tetramethylenediamine, N,N'-bis(4-methyl-aminophenyl)tetramethylenediamine, N,N'-bis(ethyl) N,N'-bis(4'-amino, 3'-methylphenyl)ethylenediamine, 1,8-bis(2,5-diaminophenoxy)-3,6-dioxaoctane, and their salts of addition.

Among the para-aminophenols, we may mention as examples: para-aminophenol, 4-amino-3-methyl phenol, 4-amino-3-fluoro phenol, 4-amino-3-chlorophenol, 4-amino-3-hydroxymethyl phenol, 4-amino-2-methyl phenol, 4-amino-2-hydroxymethyl phenol, 4-amino-2-methoxymethyl phenol, 4-amino-2-aminomethyl phenol, 4-amino-2-(β-hydroxyethyl aminomethyl)phenol, 4-amino-2-fluoro phenol, and their salts of addition with an acid.

Among the ortho-aminophenols, we may mention as examples: 2-aminophenol, 2-amino-5-methyl phenol, 2-amino-6-methyl phenol, 5-acetamido 2-aminophenol, and their salts of addition.

Among the heterocyclic bases, we may mention as examples: pyridine derivatives, pyrimidine derivatives and pyrazole derivatives.

Among the pyridine derivatives, we may mention the compounds described for example in patents GB 1 026 978 and GB 1 153 196, such as 2,5-diaminopyridine, 2-(4-methoxyphenyl)amino 3-amino pyridine, 3,4-diaminopyridine, and their salts of addition.

Other pyridine oxidation bases useful in the present invention are the 3-amino pyrazolo-[1,5-a]pyridine oxidation bases or their salts of addition described for example in patent application FR 2801308. As examples, we may mention pyrazolo[1,5-a]pyridin-3-ylamine; 2-acetylamino pyrazolo[1,5-a]pyridin-3-ylamine; 2-morpholin-4-yl-pyrazolo[1,5-a]pyridin-3-ylamine; 3-amino-pyrazolo[1,5-a]pyridine-2-carboxylic acid; 2-methoxypyrazolo[1,5-a]pyridin-3-ylamino; (3-amino-pyrazolo[1,5-a]pyridin-7-yl)methanol; 2-(3-amino-pyrazolo[1,5-a]pyridin-5-yl)ethanol; 2-(3-amino-pyrazolo[1,5-a]pyridin-7-yl)ethanol; (3-amino-pyrazolo[1,5-a]pyridin-2-yl)methanol; 3,6-diamino-pyrazolo[1,5-a]pyridine; 3,4-diamino-pyrazolo[1,5-a]pyridine; pyrazolo[1,5-a]pyridine-3,7-diamine; 7-morpholin-4-yl-pyrazolo[1,5-a]pyridin-3-ylamine; pyrazolo[1,5-a]pyridine-3,5-diamine; 5-morpholin-4-yl-pyrazolo[1,5-a]pyridin-3-ylamine; 2-[(3-amino-pyrazolo[1,5-a]pyridin-5-yl)-(2-hydroxyethyl)-amino]ethanol; 2-[(3-amino-pyrazolo[1,5-a]pyridin-7-yl)-(2-hydroxyethyl)-amino]ethanol; 3-amino-pyrazolo[1,5-a]pyridin-5-ol; 3-amino-pyrazolo[1,5-a]pyridin-4-ol; 3-amino-pyrazolo[1,5-a]pyridin-6-ol; 3-amino-pyrazolo[1,5-a]pyridin-7-ol; and the salts of addition thereof.

Among the pyrimidine derivatives, we may mention the compounds described for example in patents DE 2359399; JP 88-169571; JP 05-63124; EP 0770375 or patent application WO 96/15765 such as 2,4,5,6-tetra-aminopyrimidine, 4-hydroxy 2,5,6-triaminopyrimidine, 2-hydroxy 4,5,6-triaminopyrimidine, 2,4-dihydroxy 5,6-diaminopyrimidine, 2,5,6-triaminopyrimidine and their salts of addition and their tautomeric forms, when there is tautomeric equilibrium.

Among the pyrazole derivatives, we may mention the compounds described in patents DE 3843892, DE 4133957 and patent applications WO 94/08969, WO 94/08970, FR-A-2 733 749 and DE 195 43 988 such as 4,5-diamino 1-methyl pyrazole, 4,5-diamino 1-(β-hydroxyethyl)pyrazole, 3,4-diamino pyrazole, 4,5-diamino 1-(4'-chlorobenzyl)pyrazole, 4,5-diamino 1,3-dimethylpyrazole, 4,5-diamino 3-methyl 1-phenyl pyrazole, 4,5-diamino 1-methyl 3-phenyl pyrazole, 4-amino 1,3-dimethyl 5-hydrazino pyrazole, 1-benzyl 4,5-diamino 3-methylpyrazole, 4,5-diamino 3-tert-butyl 1-methylpyrazole, 4,5-diamino 1-tert-butyl 3-methylpyrazole, 4,5-diamino 1-(β-hydroxyethyl) 3-methylpyrazole, 4,5-diamino 1-ethyl 3-methylpyrazole, 4,5-diamino 1-ethyl 3-(4'-methoxyphenyl)pyrazole, 4,5-diamino 1-ethyl 3-hydroxymethyl pyrazole, 4,5-diamino 3-hydroxymethyl 1-methylpyrazole, 4,5-diamino 3-hydroxymethyl 1-isopropyl pyrazole, 4,5-diamino 3-methyl 1-isopropyl pyrazole, 4-amino-5-(2'-aminoethyl)amino 1,3-dimethylpyrazole, 3,4,5-triamino pyrazole, 1-methyl 3,4,5-triamino pyrazole, 3,5-diamino 1-methyl 4-methylamino pyrazole, 3,5-diamino 4-(β-hydroxyethyl)amino 1-methylpyrazole, and their salts of addition. It is also possible to use 4,5-diamino 1-(β-methoxyethyl)pyrazole.

Preferably, a 4,5-diaminopyrazole will be used, and even more preferably 4,5-diamino-1-(β-hydroxyethyl)pyrazole and/or a salt thereof.

As pyrazole derivatives, we may also mention the diamino N,N-dihydropyrazolopyrazolones and notably those described in application FR-A-2 886 136 such as the following compounds and their salts of addition: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

It is preferable to use 2,3-diamino-6,7-dihydro-1H,5H-pyrazolo[1,2-a]pyrazol-1-one and/or a salt thereof.

As heterocyclic bases, 4,5-diamino-1-(β-hydroxyethyl)pyrazole and/or 2,3-diamino-6,7-dihydro-1H,5H-pyrazolo[1,2-a]pyrazol-1-one and/or a salt thereof will preferably be used.

The composition according to the invention can optionally comprise one or more couplers selected advantageously from those used conventionally for dyeing keratin fibres.

Among these couplers, we may notably mention the meta-phenylenediamines, meta-aminophenols, meta-diphenols, naphthalenic couplers, heterocyclic couplers and their salts of addition.

As examples, we may mention 1,3-dihydroxy benzene, 1,3-dihydroxy 2-methyl benzene, 4-chloro 1,3-dihydroxy benzene, 2,4-diamino 1-(β-hydroxyethyloxy)benzene, 2-amino 4-(β-hydroxyethylamino) 1-methoxybenzene, 1,3-diamino benzene, 1,3-bis(2,4-diaminophenoxy) propane, 3-ureido aniline, 3-ureido 1-dimethylamino benzene, sesamol, 1-β-hydroxyethylamino-3,4-methylenedioxybenzene, α-naphthol, 2 methyl-1-naphthol, 6-hydroxy indole, 4-hydroxy indole, 4-hydroxy N-methyl indole, 2-amino-3-hydroxy pyridine, 6-hydroxy benzomorpholine, 3,5-diamino-2,6-dimethoxypyridine, 1-N-(β-hydroxyethyl)amino-3,4-methylene dioxybenzene, 2,6-bis(β-hydroxyethylamino) toluene, 6-hydroxy indoline, 2,6-dihydroxy 4-methylpyridine, 1-H 3-methylpyrazole 5-one, 1-phenyl 3-methylpyrazole 5-one, 2,6-dimethylpyrazolo[1,5-b]-1,2,4-triazole, 2,6-dimethyl[3,2-c]-1,2,4-triazole, 6-methylpyrazolo[1,5-a]benzimidazole, their salts of addition with an acid, and mixtures thereof.

In general, the salts of addition of the oxidation bases and of the couplers usable within the scope of the invention are notably selected from salts of addition with an acid such as hydrochlorides, hydrobromides, sulphates, citrates, succinates, tartrates, lactates, tosylates, benzenesulphonates, phosphates and acetates.

The oxidation base or bases each represent advantageously from 0.0001 to 10 wt. % relative to the total weight of the composition, and preferably from 0.005 to 5 wt. % relative to the total weight of the composition.

The content of coupler(s), if present, each represents advantageously from 0.0001 to 10 wt. % relative to the total weight of the composition, and preferably from 0.005 to 5 wt. % relative to the total weight of the composition.

The composition according to the invention can optionally comprise one or more direct dyes, synthetic or natural, selected from ionic or non-ionic species, preferably cationic or non-ionic.

As examples of direct dyes that are particularly suitable, we may mention the nitro dyes of the benzene series; the azo; azomethine and methine direct dyes; the azacarbocyanines such as tetraazacarbocyanines (tetraazapentamethines); the quinone direct dyes and in particular anthraquinone, naphthoquinone or benzoquinone direct dyes; the azine; xanthene; triarylmethane; indoamine and indigoid direct dyes; phthalocyanines, porphyrins and natural direct dyes, alone or mixed. In particular, we may mention azo; methine; carbonyl; azine; nitro(hetero)aryl; tri(hetero)aryl methane dyes; porphyrins; phthalocyanines, and natural direct dyes, alone or mixed.

Among the benzene direct dyes usable according to the invention, the following compounds may be mentioned as non-limiting examples:

1,4-diamino-2-nitrobenzene,
1-amino-2-nitro-4-β-hydroxyethylaminobenzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis(p-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-p-hydroxyethylamino-6-nitrobenzene
1-amino-2-nitro-4-p-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(p-hydroxyethyl)amino-3-nitrobenzene
1-β-hydroxyethylamino-2-nitrobenzene
1-hydroxy-4-β-hydroxyethylamino-3-nitrobenzene.

Among azo, azomethine, methine or tetraazapentamethine direct dyes usable according to the invention we may mention the cationic dyes described in patent applications WO 95/15144, WO 95/01772 and EP 714954; FR 2189006, FR 2285851, FR-2140205, EP 1378544, EP 1674073.

Thus, we may quite particularly mention the following dyes of formulae (I) to (IV), and preferably the compounds of formulae (I) and (III):

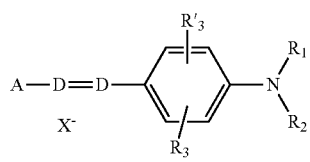
(I)

in which:

D represents a nitrogen atom or the group —CH, preferably a nitrogen atom, $R_1$ and $R_2$, identical or different, represent a hydrogen atom; a $C_1$-$C_4$ alkyl radical which can be substituted with a —CN, —OH or —NH$_2$ radical, or form with a carbon atom of the benzene ring a heterocycle optionally oxygen-containing or nitrogen-containing, which can be substituted with one or more $C_1$-$C_4$ alkyl radicals; a 4'-aminophenyl radical, $R_3$ and $R'_3$, identical or different, represent a hydrogen atom or halogen atom selected from chlorine, bromine, iodine and fluorine, a cyano, $C_1$-$C_4$ alkyl, $C_1$-$C_4$ alkoxy or acetyloxy radical, $X^-$ represents an anion preferably selected from chloride, methyl sulphate and acetate, A represents a group selected from the following structures A1 to A18, and preferably A1, A4. A7. A13 and A18:

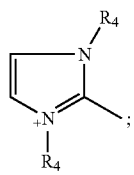
A$_1$

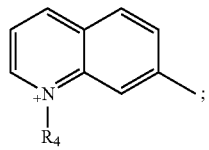
A$_2$

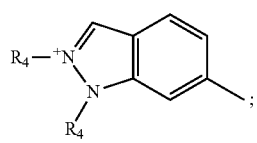
A$_3$

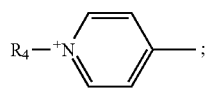
A$_4$

-continued

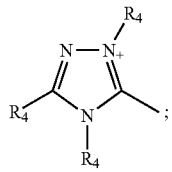
A$_5$

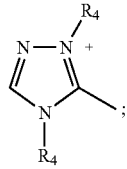
A$_6$

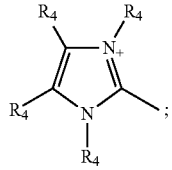
A$_7$

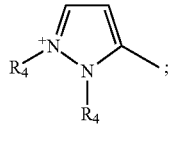
A$_8$

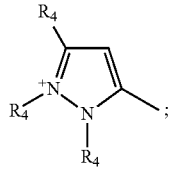
A$_9$

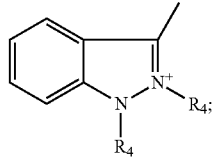
A$_{10}$

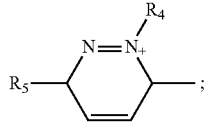
A$_{11}$

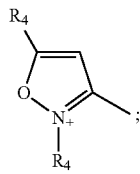
A$_{12}$

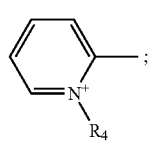
A$_{13}$

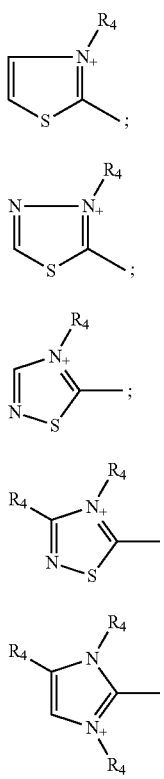

A14

A15

A16

A17

A18

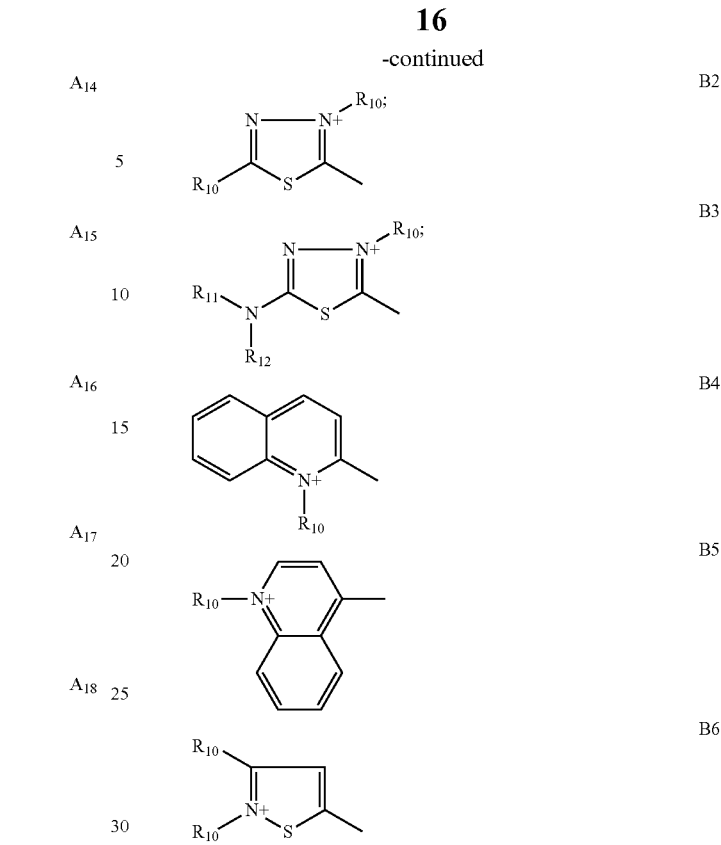

in which R₄ represents a C₁-C₄ alkyl radical which can be substituted with a hydroxyl radical and R₅ represents a C₁-C₄ alkoxy radical;

in which R₁₀ represents a C₁-C₄ alkyl radical, R₁₁ and R₁₂, identical or different, represent a hydrogen atom or a C₁-C₄ alkyl radical;

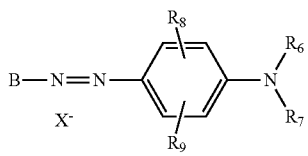

(II)

in which:
R₆ represents a hydrogen atom or a C₁-C₄ alkyl radical,
R₇ represents a hydrogen atom, an alkyl radical which can be substituted with a —CN radical or with an amino group, a 4'-aminophenyl radical or forms with R₆ a heterocycle optionally oxygen-containing and/or nitrogen-containing which can be substituted with a C₁-C₄ alkyl radical,
R₈ and R₉, identical or different, represent a hydrogen atom, a halogen atom such as bromine, chlorine, iodine or fluorine, a C₁-C₄ alkyl or C₁-C₄ alkoxy radical, a —CN radical,
X⁻ represents an anion preferably selected from chloride, methyl sulphate and acetate,
B represents a group selected from the following structures B1 to B6:

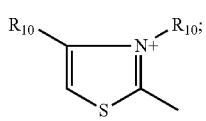

B1

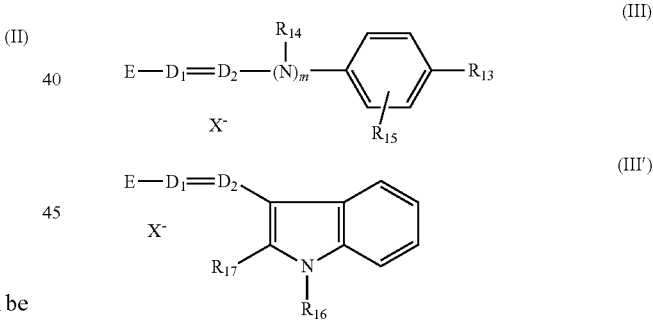

(III)

(III')

in which:
R₁₃ represents a hydrogen atom, a C₁-C₄ alkoxy radical, a halogen atom such as bromine, chlorine, iodine or fluorine,
R₁₄ represents a hydrogen atom, a C₁-C₄ alkyl radical or forms with a carbon atom of the benzene ring a heterocycle optionally oxygen-containing and/or substituted with one or more C₁-C₄ alkyl groups,
R₁₅ represents a hydrogen atom or halogen atom such as bromine, chlorine, iodine or fluorine,
R₁₆ and R₁₇, identical or different, represent a hydrogen atom or a C₁-C₄ alkyl radical,
D₁ and D₂, identical or different, represent a nitrogen atom or the group —CH, m=0 or 1,
it being understood that when R₁₃ represents an unsubstituted amino group, then D₁ and D₂ represent simultaneously a group —CH and m=0,
X⁻ represents an anion preferably selected from chloride, methyl sulphate and acetate, E represents a group selected from the following structures E1 to E8, and preferably E1, E2 and E7:

E1: R'—N⁺ pyridinium (4-methyl)

E2: 2-methylpyridinium N-R'

E3: R'—N—C(=O)—N⁺(R')— methylpyrimidinone

E4: R'—N—C(=O)—N⁺(R')— with R' on ring, methylpyrimidinone

E5: hydroxy-methyl-indazolium with N-R' and N⁺-R'

E6: benzothiazolium with N⁺-R'

E7: 3-pyridinium with N⁺-R'

E8: triazolium with R' substituents in which R' represents a $C_1$-$C_4$ alkyl radical;
when m=0 and $D_1$ represents a nitrogen atom, E can also denote a group with the following structure E9:

E9: imidazolium with R' and methyl in which R' represents a $C_1$-$C_4$ alkyl radical.

$$G-N=N-J \quad (IV)$$

in which:
the symbol G represents a group selected from the following structures $G_1$ to $G_3$:

$G_1$: pyrazolium with $R_{18}$, $R_{19}$, $R_{20}$, $R_{21}$, $X^-$ $G_2$: imidazolium/thiazolium type with $R_{18}$, $R_{20}$, $R_{21}$, Z, $X^-$ $G_3$: six-membered ring with K, M, P, $R_{23}$, $R_{24}$ and in said structures $G_1$ to $G_3$, $R_{18}$ denotes a $C_1$-$C_4$ alkyl radical, a phenyl radical which can be substituted with a $C_1$-$C_4$ alkyl radical or a halogen atom selected from chlorine, bromine, iodine and fluorine;

$R_{19}$ denotes a $C_1$-$C_4$ alkyl radical or a phenyl radical;

$R_{20}$ and $R_{21}$, identical or different, represent a $C_1$-$C_4$ alkyl radical, a phenyl radical, or form together in $G_1$ a benzene ring substituted with one or more $C_1$-$C_4$ alkyl radicals, $C_1$-$C_4$ alkoxy radicals, or $NO_2$, or form together in $G_2$ a benzene ring optionally substituted with one or more $C_1$-$C_4$ alkyl, $C_1$-$C_4$ alkoxy radicals, or $NO_2$;

$R_{20}$ can in addition denote a hydrogen atom;

Z denotes an oxygen atom, sulphur atom or a group —$NR_{19}$;

M represents a group —CH, —CR(R denoting $C_1$-$C_4$ alkyl), or —$NR_{22}(X^-)_r$;

K represents a group —CH, —CR(R denoting $C_1$-$C_4$ alkyl), or —$NR_{22}(X^-)_r$;

P represents a group —CH, —CR(R denoting $C_1$-$C_4$ alkyl), or —$NR_{22}(X^-)_r$; r denotes zero or 1;

$R_{22}$ represents an atom $O^-$, a $C_1$-$C_4$ alkoxy radical, or a $C_1$-$C_4$ alkyl radical;

$R_{23}$ and $R_{24}$, identical or different, represent a hydrogen or halogen atom selected from chlorine, bromine, iodine and fluorine, a $C_1$-$C_4$ alkyl, $C_1$-$C_4$ alkoxy radical, a radical —$NO_2$;

$X^-$ represents an anion preferably selected from chloride, iodide, methyl sulphate, ethyl sulphate, acetate and perchlorate;

provided that,
if $R_{22}$ denotes $O^-$, then r denotes zero;
if K or P or M denotes —N-alkyl $C_1$-$C_4X^-$, then $R_{23}$ or $R_{24}$ is or is not different from a hydrogen atom;
if K denotes —$NR_{22}(X^-)_r$, then M=P=—CH, —CR;
if M denotes —$NR_{22}(X^-)_r$, then K=P=—CH, —CR;
if P denotes —$NR_{22}(X^-)_r$, then K=M and denote —CH or —CR;
if Z denotes a sulphur atom with $R_{21}$ denoting $C_1$-$C_4$ alkyl, then $R_{20}$ is different from a hydrogen atom;

if Z denotes —NR$_{22}$ with R$_{19}$ denoting C$_1$-C$_4$ alkyl, then at least one of the radicals R$_{18}$, R$_{20}$ or R$_{21}$ of the group of structure G$_2$ is different from a C$_1$-C$_4$ alkyl radical;
the symbol J represents:
(a) a group with the following structure J$_1$:

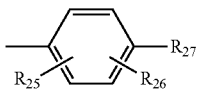

and in said structure J$_1$,
R$_{25}$ represents a hydrogen atom, a halogen atom selected from chlorine, bromine, iodine and fluorine, a C$_1$-C$_4$ alkyl, C$_1$-C$_4$ alkoxy radical, a radical —OH, —NO$_2$, —NHR$_{28}$, —NR$_{29}$R$_{30}$, C$_1$-C$_4$—NHCOalkyl, or forms with R$_{26}$ a ring with 5 or 6 ring members which may or may not contain one or more heteroatoms selected from nitrogen, oxygen or sulphur;
R$_{26}$ represents a hydrogen atom, a halogen atom selected from chlorine, bromine, iodine and fluorine, a C$_1$-C$_4$ alkyl, C$_1$-C$_4$ alkoxy radical,
or forms with R$_{27}$ or R$_{28}$ a ring with 5 or 6 ring members which may or may not contain one or more heteroatoms selected from nitrogen, oxygen or sulphur;
R$_{27}$ represents a hydrogen atom, a radical —OH, a radical —NHR$_{28}$, a radical —NR$_{29}$R$_{30}$;
R$_{28}$ represents a hydrogen atom, a C$_1$-C$_4$ alkyl radical, a C$_1$-C$_4$ monohydroxyalkyl radical, C$_2$-C$_4$ polyhydroxyalkyl, a phenyl radical;
R$_{29}$ and R$_{30}$, identical or different, represent a C$_1$-C$_4$ alkyl radical, a C$_1$-C$_4$ monohydroxyalkyl, C$_2$-C$_4$ polyhydroxyalkyl radical;
(b) a nitrogen-containing heterocyclic group with 5 or 6 ring members that can contain other heteroatoms and/or carbonylated groups and which can be substituted with one or more C$_1$-C$_4$ alkyl, amino or phenyl radicals, and notably a group with the following structure J$_2$:

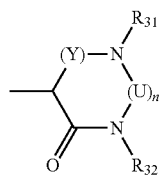

and in said structure J$_2$,
R$_{31}$ and R$_{32}$, identical or different, represent a hydrogen atom, a C$_1$-C$_4$ alkyl radical, a phenyl radical;
Y denotes the radical —CO— or the radical

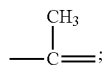

n=0 or 1, with, when n denotes 1, U denoting the radical —CO—.
In structures (I) to (IV) defined above the C$_1$-C$_4$ alkyl or alkoxy group preferably denotes methyl, ethyl, butyl, methoxy, ethoxy.

Among the compounds of formulae (I) and (III), the following compounds are preferred:

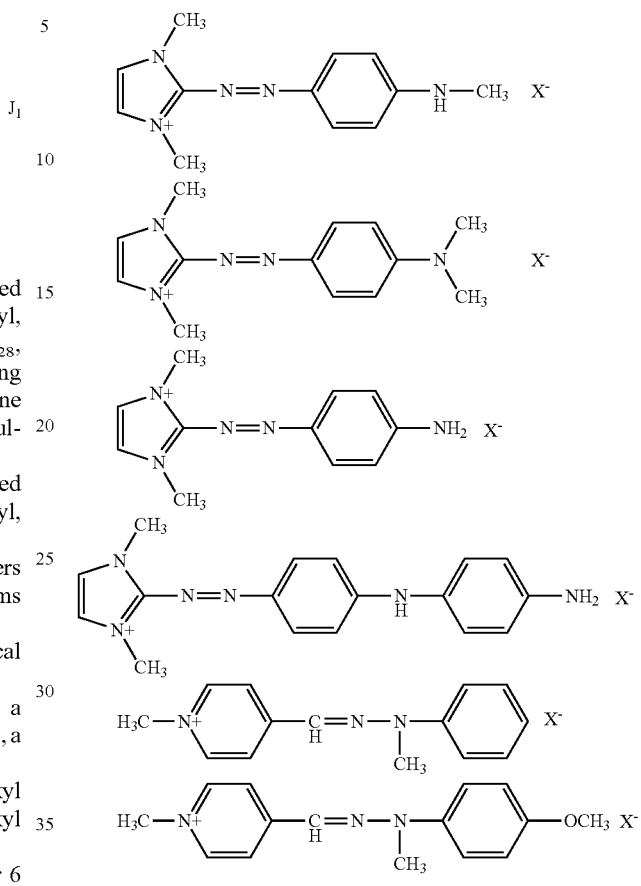

X$^-$ being defined as previously.
We may also mention, among the azo direct dyes, the following dyes, described in COLOUR INDEX INTERNATIONAL 3rd edition:
Disperse Red 17
Basic Red 22
Basic Red 76
Basic Yellow 57
Basic Brown 16
Basic Brown 17
Disperse Black 9.
We may also mention 1-(4'-aminodiphenylazo)-2-methyl-4-bis(β-hydroxyethyl)aminobenzene.
Among the quinone direct dyes, we may mention the following dyes:
Disperse Red 15
Solvent Violet 13
Disperse Violet 1
Disperse Violet 4
Disperse Blue 1
Disperse Violet 8
Disperse Blue 3
Disperse Red 11
Disperse Blue 7
Basic Blue 22
Disperse Violet 15
Basic Blue 99 as well as the following compounds:
1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine dyes, we may mention the following compounds:
Basic Blue 17
Basic Red 2.

Among the triarylmethane dyes usable according to the invention, we may mention the following compounds:
Basic Green 1
Basic Violet 3
Basic Violet 14
Basic Blue 7
Basic Blue 26

Among the indoamine dyes usable according to the invention, we may mention the following compounds:
2-β-hydroxyethlyamino-5-[bis(β-4'-hydroxyethyl)amino]anilino-1,4-benzoquinone
2-β-hydroxyethylamino-5-(2'-methoxy-4'-amino)anilino-1,4-benzoquinone
3-N-(2'-chloro-4'-hydroxy)phenylacetylamino-6-methoxy-1,4-benzoquinone imine
3-N-(3'-chloro-4'-methylamino)phenylureido-6-methyl-1,4-benzoquinone imine
3-[4'-N-(ethyl,carbamylmethyl)-amino]-phenylureido-6-methyl-1,4-benzoquinone imine.

Among the dyes of the tetraazapentamethine type usable according to the invention, we may mention the compounds shown in the following table:

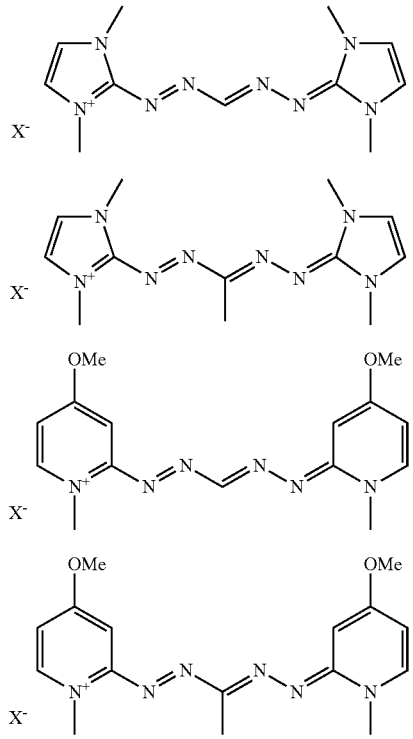

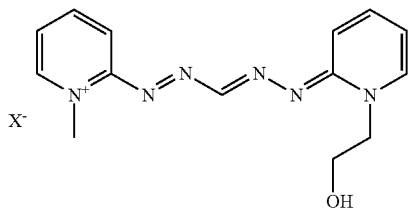

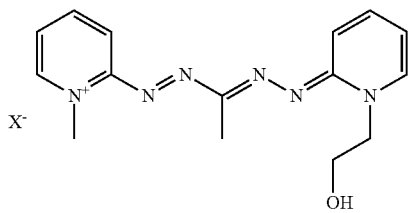

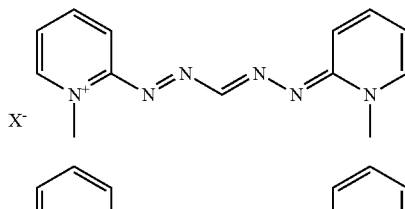

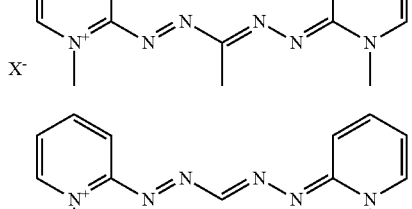

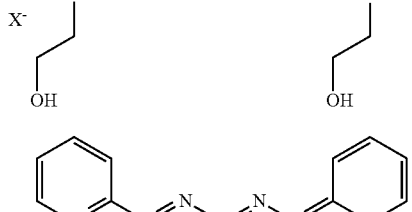

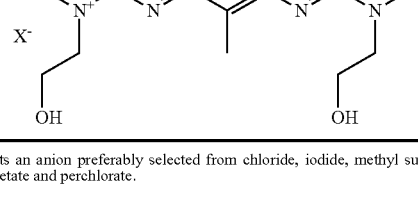

X⁻ represents an anion preferably selected from chloride, iodide, methyl sulphate, ethyl sulphate, acetate and perchlorate.

Among the natural direct dyes usable according to the invention, we may mention lawsone, juglone, alizarin, purpurin, carminic acid, kermesic acid, purpurogallin, protocatechaldehyde, indigo, isatin, curcumin, spinulosin, apigenidin, orceins. It is also possible to use extracts or decoctions containing these natural dyes and notably cataplasms or extracts based on henna.

The direct dyes can be monochromophoric dyes (i.e. only comprising a single dye) or polychromophoric, preferably di- or trichromophoric, and the chromophores can be identical or not, of the same chemical family or not. Note that a polychromophoric dye comprises several radicals each derived from a molecule absorbing in the visible region between 400 and 800 nm. Moreover, this absorbance of the dye requires neither previous oxidation of the latter, nor combination with (an) other chemical species.

In the case of polychromophoric dyes, the chromophores are joined together by at least one linkage which can be cationic or not.

Preferably, the linkage is a $C_1$-$C_{20}$ alkyl chain, linear, branched or cyclic, optionally interrupted by at least one heteroatom (such as nitrogen, oxygen) and/or by at least one group comprising same ($CO$, $SO_2$), optionally interrupted by at least one heterocycle which may or may not be condensed with a phenyl nucleus and comprising at least one quaternized nitrogen atom involved in said ring and optionally at least one other heteroatom (such as oxygen, nitrogen or sulphur), optionally interrupted by at least one phenyl or naphthyl group which may be substituted or unsubstituted, optionally interrupted by at least one quaternary ammonium group substituted with two $C_1$-$C_{15}$ alkyl groups which are optionally substituted; the linkage does not comprise a nitro, nitroso or peroxo group.

If the heterocycles or aromatic nuclei (phenyl or naphthyl) are substituted, they are substituted for example with one or more $C_1$-$C_8$ alkyl radicals optionally substituted with a hydroxy group, $C_1$-$C_2$ alkoxy group, $C_2$-$C_4$ hydroxyalkoxy group, acetylamino group, amino group substituted with one or two $C_1$-$C_4$ alkyl radicals, optionally bearing at least one hydroxyl group or the two radicals which can form, with the nitrogen atom to which they are attached, a heterocycle with 5 or 6 ring members, optionally comprising another heteroatom identical or different from nitrogen; a halogen atom; a hydroxyl group; a $C_1$-$C_2$ alkoxy radical; a $C_2$-$C_4$ hydroxyalkoxy radical; an amino radical; an amino radical substituted with one or two identical or different $C_1$-$C_4$ alkyl radicals optionally bearing at least one hydroxyl group.

Among the polychromophoric dyes, we may mention more particularly di- or tri-chromophoric azo and/or azomethine (hydrazone) dyes, symmetrical or not, comprising on the one hand at least one aromatic heterocycle comprising 5 or 6 ring members, optionally condensed, comprising at least one quaternized nitrogen atom involved in said heterocycle and optionally at least one other heteroatom (such as nitrogen, sulphur, oxygen), and on the other hand, at least one phenyl or naphthyl group, optionally substituted, optionally bearing at least one group OR with R representing a hydrogen atom, an optionally substituted $C_1$-$C_6$ alkyl radical, an optionally substituted phenyl nucleus, or bearing at least one group $N(R')_2$ with R' identical or not, representing a hydrogen atom, an optionally substituted $C_1$-$C_6$ alkyl radical, an optionally substituted phenyl nucleus; said radicals R' can form, with the nitrogen atom to which they are bound, a saturated heterocycle with 5 or 6 ring members, or else one and/or both of the radicals R' can each form, with the carbon atom of the aromatic ring positioned ortho to the nitrogen atom, a saturated heterocycle with 5 or 6 ring members.

As a cationic aromatic heterocycle, we may preferably mention rings with 5 or 6 ring members comprising 1 to 3 nitrogen atoms, preferably 1 or 2 nitrogen atoms, one being quaternized; said heterocycle being moreover optionally condensed to a benzene nucleus. It should also be noted that the heterocycle can optionally comprise another heteroatom different from nitrogen, such as sulphur or oxygen.

The bond between the linkage, as defined previously, and each chromophore is generally effected by means of a heteroatom substituting the phenyl or naphthyl nucleus or by means of the quaternized nitrogen atom of the cationic heterocycle.

The dye can comprise chromophores identical or not.

As examples of said dyes, we may notably refer to patent applications EP 1637566, EP 1619221, EP 1634926, EP 1619220, EP 1672033, EP 1671954, EP 1671955, EP 1679312, EP 1671951, EP167952, EP167971, WO 06/063866, WO 06/063867, WO 06/063868, WO 06/063869, EP 1408919, EP 1377264, EP 1377262, EP 1377261, EP 1377263, EP 1399425, EP 1399117, EP 1416909, EP 1399116, EP 1671560.

It is also possible to use cationic direct dyes mentioned in applications EP 1006153, which describes dyes comprising two chromophores of the anthraquinone type joined by a cationic linkage; EP 1433472, EP 1433474, EP 1433471 and EP 1433473 which describe dichromophoric dyes identical or not, joined together by a linkage which may or may not be cationic, as well as EP 6291333 which notably describes dyes comprising three chromophores, one of them being an anthraquinone chromophore to which are joined two chromophores of the azo or diazacarbocyanine type or an isomer thereof.

When they are present, the direct dye(s) represent more particularly from 0.0001 to 10 wt. % of the total weight of the composition, and preferably from 0.005 to 5 wt. %.

When the composition comprises direct dyes and/or oxidation dyes, the weight ratio of salified or unsalified organophosphoric acid(s) to the dye(s) is advantageously between 0.005 to 10.

The composition can optionally comprise at least one alkalizing agent.

This agent can be selected from mineral or organic or hybrid alkaline agents or mixtures thereof.

The mineral alkaline agent(s) are preferably selected from ammonia, alkaline carbonates or bicarbonates such as carbonates of sodium or of potassium and bicarbonates of sodium or of potassium, hydroxides of sodium or of potassium or mixtures thereof.

The organic alkaline agent(s) are preferably selected from organic amines whose pKb at 25° C. is below 12, and preferably below 10, even more advantageously below 6. It should be noted that it is a question of the pKb corresponding to the function with highest basicity.

As hybrid compounds, we may mention the salts of the amines mentioned previously with acids such as carbonic acid, hydrochloric acid.

It has to be noted that the alkaline agents are advantageously not compounds selected from oxidation dye precursors (bases, couplers) and direct dyes previously mentioned.

The aforementioned organic amines, whose pKb at 25° C. is below 12, are for example selected from alkanolamines, ethoxylated and/or propoxylated ethylenediamines, the amino acids and the compounds of the following formula (IX):

in which W is a $C_1$-$C_6$ alkylene residue optionally substituted with a hydroxyl group or a $C_1$-$C_6$ alkyl radical; Rx, Ry, Rz and Rt, identical or different, represent a hydrogen atom, a $C_1$-$C_6$ alkyl or $C_1$-$C_6$ hydroxyalkyl, $C_1$-$C_6$ aminoalkyl radical.

We may mention as examples of these amines, 1,3-diaminopropane, 1,3-diamino-2-propanol, spermine, spermidine.

Alkanolamine means an organic amine comprising a primary, secondary or tertiary amine function, and one or more linear or branched $C_1$-$C_8$ alkyl groups bearing one or more hydroxyl radicals.

Alkanolamines such as the mono-, di- or tri-alkanolamines, comprising one to three hydroxyalkyl radicals, identical or not, of $C_1$-$C_4$, are particularly suitable for carrying out the invention.

Among compounds of this type, we may mention monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris-hydroxymethylaminomethane.

More particularly, the amino acids that can be used are of natural or synthetic origin, in their L, D, or racemic forms and have at least one acid function selected more particularly from the carboxylic, sulphonic, phosphonic or phosphoric acid functions. The amino acids can be in the neutral or ionic form.

As amino acids usable in the present invention, we may notably mention aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising a supplementary amine function optionally included in a ring or in a ureido function.

Said basic amino acids are preferably selected from those corresponding to the following formula (X):

$$R-CH_2-CH\begin{smallmatrix}NH_2\\CO_2H\end{smallmatrix}$$ (X)

where R denotes a group selected from:

—(CH$_2$)$_2$NH$_2$ (imidazole group)

—(CH$_2$)$_2$NH—C(=NH)—NH$_2$

—(CH$_2$)$_3$NH$_2$

—(CH$_2$)$_2$NHCONH$_2$

The compounds corresponding to formula (X) are histidine, lysine, arginine, ornithine, citrulline.

The organic amine can also be selected from organic amines of the heterocyclic type. We may mention in particular, in addition to histidine already mentioned in the amino acids, pyridine, piperidine, imidazole, triazole, tetrazole, benzimidazole.

The organic amine can also be selected from the dipeptides of amino acids. As dipeptides of amino acids usable in the present invention, we may notably mention carnosine, anserine and baleine.

The organic amine is selected from the compounds having a guanidine function. As amines of this type usable in the present invention, we may notably mention in addition to arginine already mentioned as amino acid, creatine, creatinine, 1,1-dimethylguanidine, 1,1-diethylguanidine, glycocyamine, metformin, agmatine, n-amidinoalanine, 3-guanidinopropionic acid, 4-guanidinobutyric acid and 2-([amino(imino)methyl]amino)ethane-1-sulphonic acid.

As hybrid compounds we may mention in particular the use of guanidine carbonate or monoethanolamine hydrochloride.

The composition of the invention preferably contains one or more alkanolamines, and/or one or more basic amino acids, more advantageously, one or more alkanolamines.

Even more preferably the organic amine is monoethanolamine.

Advantageously, the composition according to the invention has a content of alkaline agent(s), if present, in the range from 0.01 to 30 wt. %, preferably from 0.1 to 20 wt. % relative to the weight of said composition.

When the composition comprises neither oxidation dye(s) nor direct dye(s), the weight ratio of salified or unsalified organophosphoric acid(s) to alkalizing agent(s) is preferably between 0.001 and 0.8.

In the case when the composition according to the invention comprises both one or more oxidation and/or direct dyes and one or more alkalizing agents, the weight ratio of salified or unsalified organophosphoric acid(s) to [oxidation and/or direct dye(s) and alkalizing agent(s)] is preferably between 0.0005 and 0.5.

Preferably the composition of the invention comprises one or more alkalizing agents.

The composition according to the invention also comprises one or more oxidizing agents.

More particularly, the oxidizing agent(s) are selected from hydrogen peroxide, urea peroxide, bromates or ferricyanides of alkali metals, peroxidized salts such as for example persulphates, perborates, peracids and their precursors and percarbonates of alkali metals or alkaline-earth metals.

Preferably, the oxidizing agent is not selected from the peroxidized salts.

Advantageously, the oxidizing agent is hydrogen peroxide.

The content of oxidizing agent(s) represents more particularly from 0.1 to 20 wt. %, preferably from 0.5 to 10 wt. %, relative to the weight of the composition.

The composition according to the invention can also comprise one or more surfactants.

Preferably, the surfactant(s) are selected from non-ionic surfactants or from anionic surfactants.

The anionic surfactants are more especially selected from the salts (in particular salts of alkali metals, notably of sodium, ammonium salts, salts of amines, salts of aminoalcohols or salts of alkaline-earth metals such as magnesium) of the following compounds:

alkylsulphates, alkylethersulphates, alkylamidoethersulphates, alkaryl-polyethersulphates, monoglyceride sulphates;

alkylsulphonates, alkylamidesulphonates, alkarylsulphonates, α-olefin-sulphonates, paraffin-sulphonates;

alkylphosphates, alkyletherphosphates;

alkylsulphosuccinates, alkylethersulphosuccinates, alkylamide-sulphosuccinates; alkylsulphosuccinamates;

alkylsulphoacetates;

acylsarcosinates; acylisethionates and N-acyltaurates;

salts of fatty acids such as oleic, ricinoleic, palmitic, stearic acids, acids of copra oil or of hydrogenated copra oil;

salts of alkyl D galactoside uronic acids;

acyl-lactylates;

salts of polyalkoxylated alkylether carboxylic acids, polyalkoxylated alkaryl ether carboxylic acids, polyalkoxylated alkylamidoether carboxylic acids, in particular those having from 2 to 50 ethylene oxide groups;

and mixtures thereof.

It should be noted that the alkyl or acyl radical of these various compounds advantageously has from 6 to 24 carbon atoms, and preferably from 8 to 24 carbon atoms, the aryl radical preferably denoting a phenyl or benzyl group.

The non-ionic surfactants are more particularly selected from the mono- or poly-alkoxylated, mono- or poly-glycerolated non-ionic surfactants. The alkoxylated units are more particularly ethoxylated units, propoxylated units or a combination thereof, preferably ethoxylated.

As examples of alkoxylated non-ionic surfactants, we may mention:
alkoxylated alkyl($C_8$-$C_{24}$)phenols,
alkoxylated $C_8$-$C_{30}$ alcohols, saturated or not, linear or branched,
alkoxylated $C_8$-$C_{30}$ amides, saturated or not, linear or branched,
esters of $C_8$-$C_{30}$ acids, saturated or not, linear or branched, and of polyethylene glycols,
esters of $C_8$-$C_{30}$ acids, saturated or not, linear or branched, and of polyethoxylated sorbitol,
ethoxylated vegetable oils, saturated or not,
condensates of ethylene oxide and/or of propylene oxide, among others, alone or mixed.

The surfactants have a number of moles of ethylene and/or propylene oxide between 1 and 100, preferably between 2 and 50, preferably between 2 and 30. Advantageously, the non-ionic surfactants do not comprise propoxylated units.

According to a preferred embodiment of the invention, the alkoxylated non-ionic surfactants are selected from ethoxylated $C_8$-$C_{30}$ alcohols comprising 1 to 100 moles of ethylene oxide; esters of $C_8$-$C_{30}$ acids, saturated or not, linear or branched, and of polyethoxylated sorbitol comprising 1 to 100 moles of ethylene oxide.

As examples of mono- or poly-glycerolated non-ionic surfactants, the mono- or poly-glycerolated $C_8$-$C_{40}$ alcohols are preferably used.

In particular, the mono- or poly-glycerolated $C_8$-$C_{40}$ alcohols correspond to the following formula:

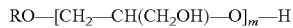

RO—[CH$_2$—CH(CH$_2$OH)—O]$_m$—H in which R represents an alkyl or alkenyl radical, linear or branched, of $C_8$-$C_{40}$, preferably of $C_8$-$C_{30}$, and m represents a number in the range from 1 to 30 and preferably from 1 to 10.

As examples of compounds that are suitable within the scope of the invention, we may mention: lauryl alcohol with 4 moles of glycerol (INCI name: POLYGLYCERYL-4 LAURYL ETHER), lauryl alcohol with 1.5 moles of glycerol, oleyl alcohol with 4 moles of glycerol (INCI name: POLYGLYCERYL-4 OLEYL ETHER), oleyl alcohol with 2 moles of glycerol (INCI name: POLYGLYCERYL-2 OLEYL ETHER), cetearyl alcohol with 2 moles of glycerol, cetearyl alcohol with 6 moles of glycerol, oleocetyl alcohol with 6 moles of glycerol, and octadecanol with 6 moles of glycerol.

The alcohol can represent a mixture of alcohols just as the value of m represents a statistical value, which signifies that a commercial product can contain several species of polyglycerolated fatty alcohols simultaneously in the form of a mixture.

Among the mono- or poly-glycerolated alcohols, it is more particularly preferable to use the $C_8$/$C_{10}$ alcohol with one mole of glycerol, the $C_{10}$/$C_{12}$ alcohol with 1 mole of glycerol and the $C_{12}$ alcohol with 1.5 mole of glycerol.

Preferably, the surfactant optionally present in the composition is a non-ionic surfactant.

The content of surfactants in the composition represents more particularly from 0.1 to 50 wt. %, preferably from 0.5 to 30 wt. % relative to the weight of the composition.

The composition can also contain various additives used conventionally in compositions for colouring or lightening the hair, such as anionic, cationic, non-ionic, amphoteric, zwitterionic polymers or mixtures thereof; antioxidants; penetrating agents; sequestering agents; perfumes; dispersants; film-forming agents; ceramides; preservatives; opacifiers.

The above additives are generally present in an amount for each of them between 0.01 and 20 wt. % relative to the weight of the composition.

The composition can comprise one or more pyrogenic silicas.

The pyrogenic silicas can be obtained by high-temperature hydrolysis of a volatile silicon compound in an oxyhydrogen flame, producing a finely divided silica. This process notably makes it possible to obtain hydrophilic silicas that have a large number of silanol groups on their surface. These hydrophilic silicas are for example marketed under the designations "AEROSIL 130®", "AEROSIL 200®", "AEROSIL 255®", "AEROSIL 300®", "AEROSIL 380®" by the company Degussa, "CAB-O-SIL HS-5®", "CAB-O-SIL EH-5®", "CAB-O-SIL LM-130®", "CAB-O-SIL MS-55®", "CAB-O-SIL M-5®" by the company Cabot.

It is possible to modify the surface of the silica chemically by chemical reaction in order to decrease the number of silanol groups. It is notably possible to replace silanol groups with hydrophobic groups: a hydrophobic silica is then obtained.

The hydrophobic groups can be:
trimethylsiloxyl groups, which are notably obtained by treatment of pyrogenic silica in the presence of hexamethyldisilazane. Silicas thus treated are called "Silica silylate" according to the CTFA (6th edition, 1995). They are for example marketed under the references "AEROSIL R812®" by the company Degussa, "CAB-O-SIL TS-530®" by the company Cabot.
dimethylsilyloxyl or polydimethylsiloxane groups, which are notably obtained by treatment of pyrogenic silica in the presence of polydimethylsiloxane or of dimethyldichlorosilane. Silicas thus treated are called "Silica dimethyl silylate" according to the CTFA (6th edition, 1995). They are for example marketed under the references "AEROSIL R972®", "AEROSIL R974®" by the company Degussa, "CAB-O-SIL TS-610®", "CAB-O-SIL TS-720®" by the company Cabot.

The pyrogenic silica preferably has a particle size that can range from nanometric to micrometric, for example in the range from about 5 to 200 nm.

When it is present, the pyrogenic silica represents from 1 to 30 wt. % relative to the weight of the composition.

The composition can also comprise one or more organic thickeners.

These thickeners can be selected from amides of fatty acids (copra diethanol- or monoethanol-amide, monoethanolamide of ethoxylated alkylether carboxylic acid), polymeric thickeners such as cellulosic thickeners (hydroxyethylcellulose, hydroxypropylcellulose, carboxymethylcellulose), guar gum and its derivatives (hydroxypropylguar), gums of microbial origin (xanthan gum, scleroglucan gum), crosslinked homopolymers of acrylic acid or of acrylamidopropanesulphonic acid and associative polymers (polymers comprising hydrophilic zones, and fatty-chain hydrophobic zones (alkyl, alkenyl comprising at least 10 carbon atoms) capable, in an aqueous environment, of associating reversibly with one another or with other molecules).

According to a particular embodiment, the organic thickener is selected from cellulosic thickeners (hydroxyethylcellulose, hydroxypropylcellulose, carboxymethylcellulose), guar gum and its derivatives (hydroxypropylguar), gums of microbial origin (xanthan gum, scleroglucan gum), crosslinked homopolymers of acrylic acid or of acrylamidopropanesulphonic acid, and preferably from cellulosic thickeners with in particular hydroxyethylcellulose.

The content of organic thickener(s), if present, usually varies from 0.01 to 20 wt. %, relative to the weight of the composition, preferably from 0.1 to 5 wt. %.

The cosmetically acceptable medium of the composition according to the invention is a medium comprising water and/or one or more organic solvents.

As organic solvent, we may for example mention monoalcohols or diols, linear or branched, preferably saturated, comprising 2 to 10 carbon atoms, such as ethyl alcohol, isopropyl alcohol, hexylene glycol (2-methyl-2,4-pentanediol), neopentylglycol and 3-methyl-1,5-pentanediol, butylene glycol, dipropylene glycol and propylene glycol; aromatic alcohols such as benzyl alcohol, phenylethyl alcohol; polyols with more than two hydroxyl functions such as glycerol; polyol ethers such as, for example, monomethyl, monoethyl and monobutyl ethers of ethylene glycol, propylene glycol or its ethers such as, for example, monomethyl ether of propylene glycol; as well as alkylethers of diethylene glycol, notably of $C_1$-$C_4$, such as for example, monoethyl ether or monobutyl ether of diethylene glycol, alone or mixed.

The organic solvents, when they are present, generally represent between 1 and 40 wt. % relative to the total weight of the dyeing composition, and preferably between 5 and 30 wt. % relative to the total weight of the dyeing composition. Preferably the composition of the invention contains water. Preferably, the concentration of water can range from 10 to 70%, more preferably from 20 to 55% of the total weight of the composition.

The dyeing composition according to the invention can be in various forms, such as in the form of liquids, creams, gels, or in any other appropriate form for carrying out dyeing of keratin fibres, and notably of hair human.

Advantageously, the composition according to the invention is in the form of a gel or a cream.

The pH of the composition according to the invention is advantageously between 3 and 12, preferably between 5 and 11. Preferably between 7 and 11 inclusive.

It can be adjusted to the desired value by means of acidifying or alkalizing agents usually employed in the dyeing of keratin fibres.

The alkalizing agents are for example those described previously.

Among acidifying agents, we may mention, as examples, mineral or organic acids such as hydrochloric acid, orthophosphoric acid, carboxylic acids such as tartaric acid, citric acid, lactic acid, or sulphonic acids.

The composition of the invention can be obtained by mixing at least two different compositions, or even three or optionally more than three different compositions. One or more of the compositions leading by mixing to the composition of the invention can be anhydrous. Note that the composition according to the invention is prepared just before it is applied on human keratin fibres.

According to a first variant, the composition according to the invention is obtained by mixing a first composition comprising one or more fatty substances, one or more oxidation dyes, direct dyes or a mixture thereof and/or one or more alkalizing agents, with a second composition comprising one or more oxidizing agents, the first and/or second composition comprising one or more salified or unsalified organophosphonic acids.

According to a second variant of the invention, the composition according to the invention is obtained by mixing a first composition comprising one or more fatty substances, a second composition comprising one or more oxidation dyes, direct dyes or mixtures thereof and/or one or more alkalizing agents, and a third composition comprising one or more oxidizing agents; the first and/or second and/or third composition comprising one or more salified or unsalified organophosphonic acids.

The ingredients of the aforementioned compositions and their contents are determined depending on the characteristics given in detail previously for the final composition according to the invention.

In each of the aforementioned variants, the oxidizing composition is preferably an aqueous composition. In particular, it comprises more than 5 wt. % of water, preferably more than 10 wt. % of water, and even more advantageously more than 20 wt. % of water.

It can also comprise one or more organic solvents selected from those listed previously; the latter representing more particularly, when they are present, from 1 to 40 wt. % relative to the weight of the oxidizing composition, and preferably from 5 to 30 wt. %.

The oxidizing composition preferably also comprises one or more acidifying agents. Among acidifying agents, we may mention as examples: mineral or organic acids such as hydrochloric acid, orthophosphoric acid, sulphuric acid, carboxylic acids such as acetic acid, tartaric acid, citric acid, lactic acid, sulphonic acids.

Usually, the pH of the oxidizing composition, when it is aqueous, is below 7.

Preferably, the oxidizing composition comprises hydrogen peroxide as the oxidizing agent, in aqueous solution, the concentration of which varies, more particularly, from 0.1 to 50%, more particularly between 0.5 and 20%, and even more preferably between 1 and 15 wt. % relative to the weight of the oxidizing composition.

The method of colouring according to the invention therefore consists in applying the composition according to the invention on dry or wet human keratin fibres.

The composition is then left in place for a time usually ranging from one minute to one hour, preferably from 5 minutes to 30 minutes.

The temperature during the procedure is conventionally between room temperature (between 15 and 25° C.) and 80° C., preferably between room temperature and 60° C.

At the end of the treatment, the human keratin fibres are optionally rinsed with water, optionally washed with a shampoo followed by a water rinse, before being dried or left to dry.

The invention also relates to a two-compartment kit containing, in one compartment, a first composition comprising one or more fatty substances, one or more alkalizing agents and/or one or more dyes selected from oxidation dyes, direct dyes or mixtures thereof; in the other compartment, a second composition comprising one or more oxidizing agents; the first and/or second composition comprising one or more salified or unsalified organophosphonic acids, the compositions of the two compartments being intended to be mixed to give the composition according to the invention, just before application on human keratin fibres.

The invention finally relates to a three-compartment kit containing, in one compartment, a first composition comprising one or more fatty substances; in another compartment, a second composition comprising one or more alkalizing agents and/or one or more dyes selected from oxidation dyes, direct dyes or mixtures thereof; and in the last compartment, a third composition comprising one or more oxidizing agents; the first and/or second and/or third composition comprising one or more salified or unsalified organophosphonic acids; the compositions of the three compartments being intended to be mixed to give the composition according to the invention, just before application on human keratin fibres.

The following examples serve to illustrate the invention although without limiting it.

EXAMPLES

The following compositions are prepared (the quantities are expressed in g % of active substances)

Composition 1

| | |
|---|---|
| Disteardimonium hectorite (Bentone 38 VCG) | 3 |
| Octyldodecanol | 11.5 |
| Glycol distearate | 8 |
| Liquid paraffin | 64.5 |
| Propylene carbonate | 1 |
| Laureth-2 | 1 |
| Polysorbate 21 | 11 |

Composition 2

| | |
|---|---|
| 1- Hydroxy ethylidene-1,1-diphosphonic acid (etidronic acid), tetrasodium salt | 0.4 |
| Sodium metabisulphite | 0.7 |
| Monoethanolamine | 14.5 |
| Toluene-2,5-diamine | 2.25 |
| 2,4-Diaminophenoxyethanol hydrochloride | 0.05 |
| Resorcinol | 2 |
| m-Aminophenol | 0.36 |
| Hydroxyethylcellulose (Natrosol 250 HHR, Aqualon) | 1.5 |
| Hexylene glycol | 3 |
| Dipropylene glycol | 3 |
| Ethanol | 8.25 |
| Propylene glycol | 6.2 |
| Ascorbic acid | 0.25 |
| Water | Qsf 100 |

Composition 3

| | |
|---|---|
| 1-Hydroxy ethylidene-1,1-diphosphonic acid (etidronic acid), tetrasodium salt | 0.06 |
| Hydrogen peroxide (50% aqueous solution) | 12 |
| Sodium stannate | 0.04 |
| Phosphoric acid | Qs pH 2.2 |
| Tetrasodium pyrophosphate | 0.03 |
| Liquid paraffin | 20 |
| Tetramethyl hexamethylenediamine/dichloro-1,3-propylene polycondensate (40% aqueous solution; Hexadimethrine chloride) | 0.1 |
| Polydimethyl diallyl ammonium chloride (40% aqueous solution, unstabilized, Polyquaternium-6) | 0.2 |
| Glycerol | 0.5 |
| Cetylstearyl alcohol (C16/C18 30/70 - NAFOL 1618F) | 8 |
| Ethoxylated cetylstearyl alcohol (33 EO) | 3 |
| Ethoxylated amide of colza acids (4 EO) | 1.2 |
| Vitamin E: DL-α-tocopherol | 0.1 |
| Water | Qsf 100 |

Method of Application

The three compositions detailed above are mixed at the moment of use in the following proportions:
10 g of composition 1
4 g of composition 2
16 g of composition 3.

The resulting mixture is then applied on locks of natural hair at 90% white, at the rate of 10 g of mixture to 1 g of hair.

The mixture is left at room temperature for 30 minutes.

The hair is then rinsed, washed with a standard shampoo and dried.

Locks of a light chestnut colour are obtained (visual evaluation).

The invention claimed is:

1. A composition comprising:
   (a) at least about 25 wt. % of at least one fatty substance;
   (b) at least one salified or unsalified organophosphonic acid or salt thereof;
   (c) at least one alkalizing agent and/or at least one dye chosen from oxidation dyes, direct dyes, and mixtures thereof; and
   (d) at least one oxidizing agent.

2. The composition of claim 1, wherein the at least one fatty substance is chosen from liquid and pasty compounds.

3. The composition of claim 1, wherein the at least one fatty substance is chosen from $C_6$-$C_{16}$ lower alkanes, non-silicone oils of synthetic origin, hydrocarbons of mineral or synthetic origin, fatty alcohols, and mixtures thereof.

4. The composition of claim 1, wherein the at least one fatty substance is chosen from liquid paraffin, polydecenes, liquid esters of fatty acids and/or fatty alcohols, liquid fatty alcohols, and mixtures thereof.

5. The composition of claim 1, wherein the at least one fatty substance is present in an amount ranging from about 25 wt. % to about 80 wt. %, relative to the total weight of the composition.

6. The composition of claim 5, wherein the at least one fatty substance is present in an amount ranging from about 30 wt. % to about 55 wt. %, relative to the total weight of the composition.

7. The composition of claim 1, wherein the at least one salified or unsalified organophosphonic acid or salt thereof is chosen from compounds having at least two —P(OH)$_2$=O groups in their structure.

8. The composition of claim 1, wherein the at least one salified or unsalified organophosphonic acid is chosen from 1-hydroxy ethylidene-1,1-diphosphonic acid.

9. The composition of claim 1, wherein the at least one salified or unsalified organophosphonic acid or salt thereof is present in an amount ranging from about 0.001 wt. % to about 10 wt. %, relative to the total weight of the composition.

10. The composition of claim 9, wherein the at least one salified or unsalified organophosphonic acid or salt thereof is present in an amount ranging from about 0.002 wt. % to about 1 wt. %, relative to the total weight of the composition.

11. The composition of claim 1, wherein the at least one oxidation dye is chosen from oxidation bases chosen from para-phenylenediamines, bisphenylalkylenediamines, para-aminophenols, ortho-aminophenols, heterocyclic bases, and their salts of addition.

12. The composition of claim 1, further comprising at least one coupler chosen from meta-phenylenediamines, meta-aminophenols, meta-diphenols, naphthalenic couplers, heterocyclic couplers and their salts of addition.

13. The composition of claim 1, wherein the at least one alkalizing agent is chosen from mineral alkaline agents, organic alkaline agents, and hybrid alkaline agents.

14. The composition of claim 13, wherein the mineral alkaline agents are chosen from ammonia, alkali metal carbonates or bicarbonates, and hydroxides of sodium or of potassium.

15. The composition of claim 13, wherein the organic alkaline agents are chosen from organic amines whose pKb at about 25° C. is below about 12, organic amines whose pKb at about 25° C. is below about 10, and organic amines whose pKb at about 25° C. is below about 6.

16. The composition of claim 15, wherein the hybrid alkaline agents are chosen from salts of the organic amines with carbonic acid and salts of the organic amines with hydrochloric acid.

17. The composition of claim 1, further comprising at least one alkanolamine, at least one basic amino acid, or mixtures thereof.

18. The composition of claim 1, further comprising monoethanolamine.

19. A method of coloring or lightening human keratin fibers comprising steps of:
   (1) applying to said human keratin fibers a composition comprising:
      (a) at least about 25 wt. % of at least one fatty substance;
      (b) at least one salified or unsalified organophosphonic acid or salt thereof;
      (c) at least one alkalizing agent and/or at least one dye chosen from oxidation dyes, direct dyes, and mixtures thereof; and
      (d) at least one oxidizing agent; and
   (2) optionally rinsing the keratin fibers.

20. A kit comprising:
   a first compartment containing a first composition comprising:
      at least about 25 wt. % of at least one fatty substance;
      at least one alkalizing agent and/or at least one dye chosen from oxidation dyes, direct dyes, and mixtures thereof;
   a second compartment containing a second composition comprising:
      at least one oxidizing agent; and
   the first and/or the second composition further comprising at least one salified or unsalified organophosphonic acid or salt thereof, wherein the first and the second compositions of the first and second compartments are configured to be mixed just before application to human keratin fibers.

21. A kit comprising:
   a first compartment containing a first composition comprising:
      at least about 25 wt. % of at least one fatty substance;
   a second compartment containing a second composition comprising:
      at least one alkalizing agent and/or at least one dye chosen from oxidation dyes, direct dyes, and mixtures thereof;
   a third compartment containing a third composition comprising:
      at least one oxidizing agent; and
   the first and/or second and/or third composition further comprising at least one salified or unsalified organophosphonic acid or salt thereof, wherein the first, second and third compositions of the first, second and third compartments are configured to be mixed just before application to human keratin fibers.

* * * * *